(12) United States Patent
Ugwu et al.

(10) Patent No.: US 7,674,790 B2
(45) Date of Patent: Mar. 9, 2010

(54) PROCESSES OF MAKING AND USING PHARMACEUTICAL FORMULATIONS OF ANTINEOPLASTIC AGENTS

(75) Inventors: Sydney Ugwu, Wheeling, IL (US); Vinay Radhakrishnan, Laurence Harbor, NJ (US); Peter M. Ihnat, Brooklyn, NY (US); Leonore C. Witchey-Lakshmanan, Piscataway, NJ (US)

(73) Assignee: Schering Corporation, Kenilworth, NJ (US)

( * ) Notice: Subject to any disclaimer, the term of this patent is extended or adjusted under 35 U.S.C. 154(b) by 659 days.

(21) Appl. No.: 11/332,721

(22) Filed: Jan. 13, 2006

(65) Prior Publication Data

US 2006/0122163 A1 Jun. 8, 2006

Related U.S. Application Data

(62) Division of application No. 10/371,808, filed on Feb. 21, 2003, now Pat. No. 6,987,108.

(60) Provisional application No. 60/359,198, filed on Feb. 22, 2002.

(51) Int. Cl.
*A61K 31/53* (2006.01)
*A61K 31/415* (2006.01)
*A61K 31/16* (2006.01)

(52) U.S. Cl. .................. 514/243; 514/396; 514/613

(58) Field of Classification Search .................. 514/183, 514/243, 396, 613
See application file for complete search history.

(56) References Cited

U.S. PATENT DOCUMENTS

| 4,455,256 A | 6/1984 | Urist |
| 4,675,183 A | 6/1987 | Kato et al. |
| 5,227,373 A | 7/1993 | Alexander et al. |
| 5,260,291 A * | 11/1993 | Lunt et al. .................. 514/183 |
| 5,268,368 A * | 12/1993 | Palepu ......................... 514/110 |
| 5,731,304 A | 3/1998 | Baer et al. |
| 6,251,886 B1 | 6/2001 | Friedman |
| 6,803,365 B2 | 10/2004 | Niewohner et al. |
| 2004/0043001 A1 | 3/2004 | Ugwu et al. |
| 2006/0100188 A1 | 5/2006 | Zong et al. |

FOREIGN PATENT DOCUMENTS

| EP | 0653210 A | 5/1995 |
| JP | 63 313721 | 12/1988 |
| SU | 1 479 049 | 5/1989 |

OTHER PUBLICATIONS

Marzolini, C., et al., "Pharmacokinetics of temozolomide in association with fotemustine in malignant melanoma and malignant glioma patients: Comparison of oral, intravenous, and hepatic intra-arterial administration" Cancer Chemotherapy and Pharmacology, vol. 42, No. 6, pp. 433-440, (1998).
Slack, A.J., et al., "Phase I clinical pharmacokinetics of temozolomide (CCRG81045, NSC362856)" Proceedings of the American Association for Cancer Research, vol. 30, p. 250, Abstract 993 (1989).
Sampson, J.H., "Treatment of Neoplastic Meningitis with Intrathecal Temozolomide", Clinical Cancer Research, vol. 5, pp. 1183-1188 (1999).
Baker, S.D., "Absorption, Metabolism, and Excretion of $^{14}$C-Temozolomide following oral Administration to Patients with Advanced Cancer", Clinical Cancer Research, vol. 5, pp. 309-317 (1999).
Saad, W., "Temozolomide Powder for Injection Pharmaceutical Development Report", Schering-Plough Research Institute.
Stability Report: Temozolomide Powder for Injection (excerpt from EMEA submission).

* cited by examiner

*Primary Examiner*—Kevin Weddington

(57) ABSTRACT

In its several embodiments, this invention discloses a pharmaceutical formulation comprising at least one antineoplastic agent or a pharmaceutically acceptable salt thereof, and at least one dissolution enhancing agent sufficient to substantially dissolve said at least one antineoplastic agent in at least one aqueous diluent, wherein said dissolution enhancing agent is urea, L-histidine, L-threonine, L-asparagine, L-serine, L-glutamine or mixtures thereof; a lyophilized powder comprising said pharmaceutical formulation, and articles of manufacture thereof.

19 Claims, No Drawings

PROCESSES OF MAKING AND USING PHARMACEUTICAL FORMULATIONS OF ANTINEOPLASTIC AGENTS

This application is a divisional application of U.S. Ser. No. 10/371,808 filed Feb. 21, 2003, now allowed, which claims the benefit of U.S. Ser. No. 60/359,198 filed Feb. 22, 2002, the entirety of which are incorporated by reference as if set forth fully herein.

FIELD OF THE INVENTION

The present invention pertains to pharmaceutical formulations comprising antineoplastic agents, such as Temozolomide, and dissolution enhancing agents.

BACKGROUND OF INVENTION

Antineoplastic agents are useful in cancer therapies against a wide array of cancer and other diseases. Temozolomide is one such antineoplastic agent. U.S. Pat. No. 6,096,759 lists a variety of antineoplastic agents including Temozolomide, the disclosure of which is incorporated herein by reference.

Temozolomide is known for its anti-tumor effects. For example, one study showed that clinical responses were achieved in 17% of patients having advanced melanoma (Newlands E S, et al. *Br J Cancer* 65 (2) 287-2981 (1992)). In another study, a clinical response was achieved in 21% of patients with advanced melanoma (*Journal of Clinical Oncology*, 13(4) 910-913 (1995)). Treatment of gliomas in adults with Temozolomide is also known (*Eur. J. Cancer* 29A 940 (1993)). Treatment of the following cancers in adults with Temozolomide has also been disclosed: metastatic melanoma; malignant melanoma, high grade glioma, glioblastoma and other brain cancers; lung cancer; breast cancer; testicular cancer; colon and rectal cancers; carcinomas; sarcomas; lymphomas; leukemias; anaplastic astrocytoma; and mycosis fungoides.

Temozolomide is a water-insoluble compound. Temozolomide has been administered in patients as micronized suspensions, as disclosed in U.S. Pat. No. 6,251,886. However, suspension formulations are not desirable because they may lead to clogged veins.

Storage of pharmaceutical and biological agents, especially antineoplastic agents, as a frozen solution can cause the active ingredient therein to rapidly deteriorate.

Lyophilization, also known as freeze-drying, is a process whereby water is sublimed from a composition after it is frozen. In this process, pharmaceutical and biological agents that are relatively unstable in an aqueous solution over a period of time can be placed into dosage containers in an easily processed liquid state, dried without the use of damaging heat and stored in a dried state for extended periods. Most pharmaceutical and biological agents, including antineoplastic agents, require additional ingredients to protect the active ingredient during lyophilization. In addition, it can be difficult to reconstitute a lyophilized antineoplastic agent into an aqueous solution.

Accordingly there is an increased need for formulations containing antineoplastic agents, such as Temozolomide, which are water soluble, stable and/or suitable for lyophilization, long term storage and reconstitution of the lyophilized formulation into an aqueous solution.

Furthermore, there is an increased need for administering to a patient an antineoplastic agent, such as Temozolomide, as a water soluble and stable formulation.

SUMMARY OF THE INVENTION

This invention relates to pharmaceutical formulations comprising at least one antineoplastic agent, processes of making the same, processes of lyophilization of the pharmaceutical formulations, lyophilized powders and articles of manufacture thereof, pharmaceutical formulations comprising the lyophilized powder reconstituted in at least one aqueous diluent, and processes of treating or preventing diseases comprising administering the pharmaceutical formulation to an animal in need thereof.

One aspect of the invention relates to a pharmaceutical formulation comprising at least one antineoplastic agent or a pharmaceutically acceptable salt thereof, at least one aqueous diluent, and at least one dissolution enhancing agent sufficient to substantially dissolve said antineoplastic agent(s), wherein said dissolution enhancing agent is urea, L-histidine, L-threonine, L-asparagine, L-serine, L-glutamine or mixtures thereof.

Another aspect of the invention relates to a process for making the pharmaceutical formulation of the invention. This process comprises the steps of dissolving at least one dissolution enhancing agent in at least one aqueous diluent, and adding at least one antineoplastic agent or a pharmaceutically acceptable salt thereof.

Another aspect of the invention relates to a lyophilized powder produced by lyophilization of the pharmaceutical formulation of the invention.

Another aspect of the invention relates to an article of manufacture comprising a container containing the lyophilized powder of the invention.

Another aspect of the invention relates to a pharmaceutical formulation suitable for administration to a patient, wherein the formulation is prepared by reconstituting (resolubilizing) the lyophilized powder of the invention in a volume of water or other aqueous diluent.

Another aspect of the invention relates to a process for treating or preventing diseases in patients comprising administering a therapeutically effective amount of the pharmaceutical formulation of the invention to a patient in need thereof.

Other aspects of this invention relate to and disclose pharmaceutical formulations of Temozolomide, a process of making the same, a lyophilized powder of said formulation and articles of manufacture thereof, a pharmaceutical formulation comprising the lyophilized powder reconstituted in water or other aqueous diluents, and a process of treating or preventing diseases (such as, for example, cancer) comprising administering the pharmaceutical formulation to a patient in need thereof.

DETAILED DESCRIPTION

The pharmaceutical formulation of the invention comprises at least one antineoplastic agent or a pharmaceutically acceptable salt thereof, at least one aqueous diluent, and at least one dissolution enhancing agent sufficient to substantially dissolve the antineoplastic agent in the aqueous diluent(s). The percentage of the antineoplastic agent which is dissolved in the pharmaceutical formulation can range from about 50% to about 100%, preferably from about 75% to about 100%, and more preferably about 100%.

The dissolution enhancing agent is urea, L-histidine, L-threonine, L-asparagine, L-serine, L-glutamine or mixtures thereof. The dissolution enhancing agent increases the rate in which the antineoplastic agent dissolves in the aqueous diluent(s). The time to it takes to complete dissolution of at least one antineoplastic agent with a dissolution agent in at least one aqueous diluent in a 25 mg vial can range from about 30 seconds to about 90 seconds, preferably from about 30 seconds to about 60 seconds, more preferably about 30 seconds.

When urea is used in the pharmaceutical formulation as the dissolution enhancing agent, its weight percent (wt %) in the pharmaceutical formulation can range from about 4 wt % to about 60 wt %, preferably from about 8 wt % to about 30 wt %, more preferably from about 12 wt % to about 22 wt %.

When L-histidine, L-threonine, L-asparagine, L-serine, L-glutamine or mixtures thereof are used in the pharmaceutical formulation as the dissolution enhancing agent(s), its wt % in the pharmaceutical formulation can range from about 2 wt % to about 60 wt %, preferably from about 4 wt % to about 40 wt %, more preferably from about 8 wt % to about 20 wt %.

When L-histidine is the only amino acid used in the pharmaceutical formulation as the dissolution enhancing agent, its wt % in the pharmaceutical formulation can range preferably from about 1 wt % to about 30 wt %, more preferably from about 2 wt % to about 20 wt %, and most preferably from about 4 wt % to about 10 wt %.

Non-limiting examples of useful antineoplastic agents include Temozolomide (commercially available under the trademark TEMODAR® from Schering-Plough Corporation, Kenilworth, N.J.), Uracil Mustard, Chlormethine, Cyclophosphamide, Ifosfamide, Melphalan, Chlorambucil, Pipobroman, Triethylenemelamine, Triethylenethiophosphoramine, Busulfan, Carmustine, Lomustine, Streptozocin, Dacarbazine, Methotrexate, 5-Fluorouracil, Floxuridine, Cytarabine, 6-Mercaptopurine, 6-Thioguanine, Fludarabine phosphate, Pentostatine, Gemcitabine, Vinblastine, Vincristine, Vindesine, Bleomycin, Dactinomycin, Daunorubicin, Doxorubicin, Epirubicin, Idarubicin, Paclitaxel, Mithramycin, Deoxycoformycin, Mitomycin-C, L-Asparaginase, Interferons, Etoposide, Teniposide 17.alpha.-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlortrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, and mixtures thereof.

In a preferred embodiment, at least one of the antineoplastic agents is Temozolomide.

In another preferred embodiment, the antineoplastic agent is a therapeutically effective amount of Temozolomide.

The wt % of the antineoplastic agent in the pharmaceutical formulation can range from about 1 wt % to about 50 wt %, preferably from about 2 wt % to about 30 wt %, more preferably from about 4 wt % to about 16 wt %.

In another embodiment, the pharmaceutical formulation further comprises at least one excipient. Non-limiting examples of suitable excipients include polysorbates, polyethylene glycols (PEG), propylene glycols, polysorbates or suitable mixtures thereof. The excipient is used to increase the solubility of the antineoplastic agent.

The average molecular weight of polysorbates can range from about 500 g/mole to about 1900 g/mole, preferably from about 800 g/mole to about 1600 g/mole, more preferably from about 1000 g/mole to about 1400 g/mole. Non-limiting examples of polysorbates include polysorbate 20, polysorbate 21, polysorbate 40, polysorbate 60, polysorbate 61, polysorbate 65, polysorbate 81, polysorbate 85, and polysorbate 120. Preferred polysorbates include polysorbate 20, polysorbate 80, and mixtures thereof.

The average molecular weight of PEG can range from about 200 g/mole to about 600 g/mole, preferably from about 200 g/mole to about 500 g/mole, more preferably from about 200 g/mole to about 400 g/mole. Non-limiting examples include PEG 200, PEG 300, PEG 400, PEG 540, and PEG 600.

Propylene glycol is a small molecule with a molecular weight of about 76.1 g/mole.

When an excipient is used in the pharmaceutical formulation, its wt % in the pharmaceutical formulation can range from about 1 wt % to about 50 wt %, preferably from about 2 wt % to about 30 wt %, more preferably from about 4 wt % to about 16 wt %.

In another embodiment, the pharmaceutical formulation further comprises at least one bulking agent. Non-limiting examples of suitable bulking agents which can be included in the pharmaceutical formulation include mannitol, lactose, sucrose, sodium chloride, trehalose, dextrose, starch, hydroxyethylstarch (hetastarch), cellulose, cyclodextrins, glycine, or mixtures thereof.

In a preferred embodiment, the bulking agent in the pharmaceutical formulation is mannitol.

When a bulking agent is used in the pharmaceutical formulation, its wt % in the pharmaceutical formulation can range from about 20 wt % to about 80 wt %, preferably from about 35 wt % to about 65 wt %, more preferably from about 40 wt % to about 56 wt %.

In another embodiment, the pharmaceutical formulation further comprises at least one buffer.

Non-limiting examples of suitable buffers which can be included in the pharmaceutical formulation include citrate buffers, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, or mixtures thereof.

Preferably, a buffer used in the pharmaceutical formulation is at least one citrate buffer. Non-limiting examples of suitable citrate buffers include lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, or calcium citrate heptahydrate.

When a buffer is used in the pharmaceutical formulation, its wt % in the pharmaceutical formulation can range from about 5 wt % to about 60 wt %, preferably from about 10 wt % to about 40 wt %, more preferably from about 15 wt % to about 28 wt %.

In another embodiment, the pharmaceutical formulation further comprises a pH adjuster. Non-limiting examples of suitable pH adjusters which can be included in the pharmaceutical formulation are hydrochloric acid, sodium hydroxide, citric acid, phosphoric acid, lactic acid, tartaric acid, succinic acid, or mixtures thereof.

A preferred pH adjuster for the pharmaceutical formulation is hydrochloric acid.

When a pH adjuster is used in the pharmaceutical formulation, its wt % in the pharmaceutical formulation can range from about 1 wt % to about 20 wt %, preferably from about 2 wt % to about 12 wt %, more preferably from about 4 wt % to about 8 wt %.

The pH of the pharmaceutical formulation preferably ranges from about 2.5 to about 6.0, more preferably from about 3.0 to about 4.5, and most preferably from about 3.8 to about 4.2.

The pharmaceutical formulation and the lyophilized powders thereof can be stored in containers commonly used in the pharmaceutical industry, which can include plastic containers or glass containers such as standard USP Type I borosilicate glass containers. For example, the container used can be a syringe or vial.

Another aspect of the invention relates to a process for making the pharmaceutical formulation of the invention. This process comprises the steps of dissolving at least one dissolution enhancing agent in at least one aqueous diluent, and adding at least one antineoplastic agent or a pharmaceutically acceptable salt thereof, preferably in that order. In the ideal embodiment, the antineoplastic agent is added after the dissolution enhancing agent is completely dissolved. The dissolution enhancing agent can be urea, L-histidine, L-threonine, L-asparagine, L-serine, L-glutamine or mixtures thereof. The volume of aqueous diluent(s) preferably comprises at least 80% of the total volume.

In another embodiment, the process further comprises adding at least one bulking agent; adding at least one buffer; and adding at least one pH adjuster to form a solution; preferably in that order, and filtering the solution.

In another embodiment, the process further comprises filling the filtered solution into a lyophilization container and lyophilizing the solution contained within the lyophilization container to produce a lyophilized powder. 'Lyophilized powders' for purposes of this invention is meant to include all lyophilized forms including lyophilized cakes.

The moisture content of the lyophilized powders can range from to about 0.1% to about 3%, preferably from about 0.2% to about 0.8%, more preferably from about 0.2% to about 0.6%. Moisture content can be measured by a moisture analyzer; many suitable moisture analyzers are commercially available.

Lyophilization is a process whereby water is sublimed from a formulation after it is frozen. In this process, pharmaceutical and biological agents that are relatively unstable in an aqueous solution over a period of time can be placed into dosage containers in an easily processed liquid state, dried without the use of damaging heat, and stored in a dried state for extended periods.

Another aspect of the invention relates to lyophilized powders produced by lyophilization of the pharmaceutical formulation of the invention.

Another aspect of the invention relates to an article of manufacture comprising a container containing the lyophilized powder produced by the lyophilization of the pharmaceutical formulation of the invention. Suitable containers are discussed above. In a preferred embodiment, the article of manufacture contains a therapeutically effective amount of the antineoplastic agent(s) in a lyophilized powder.

In another embodiment, the article of manufacture further comprises a volume of at least one aqueous diluent for reconstitution of the lyophilized powder. Reconstitution time generally takes from about 30 seconds to about 60 seconds.

Another aspect of the invention relates to a pharmaceutical formulation suitable for administration to a patient, said formulation prepared by reconstituting (resolubilizing) the lyophilized powder of the invention in a volume of at least one aqueous diluent.

The lyophilized formulations of the pharmaceutical formulations can be diluted or reconstituted prior to administration with a suitable aqueous diluent(s) to obtain a finished concentration. For example, a concentration of from about 0.5 mg/ml to about 5 mg/ml, preferably from about 1 mg/ml to about 3 mg/ml, and more preferably from about 2 mg/ml to about 3 mg/ml is suitable for transfer to an infusion bag for use by a patient in need of an antineoplastic agent such as Temozolomide.

Another aspect of the invention relates to a process for treating or preventing disease in a patient comprising administering a therapeutically effective amount of the pharmaceutical formulation of the invention to a patient in need thereof. The pharmaceutical formulation in this aspect of the invention can be a formulation which are the lyophilized powders reconstituted with water or other aqueous diluents, or the formulations which are not prepared by reconstituting the lyophilized powders. Non-limiting examples of diseases which can be treated or prevented include carcinoma, sarcoma, melanoma, glioma, glioblastoma, brain cancer, lung cancer, thyroid follicular cancer, pancreatic cancer, breast cancer, anaplastic astrocytoma, bladder cancer, myelodysplasia, prostate cancer, testicular cancer, colon and rectal cancer, lymphoma, leukemia, or mycosis fungoides.

The dosage regimen utilizing the pharmaceutical formulations of the invention is selected based upon consideration of a variety of factors, including species, age, weight, sex and medical condition of the patient; the specific disease to be treated, the severity of the condition to be treated; the route of administration; the renal and hepatic function of the patient; and the particular active ingredient or salt thereof employed. An ordinarily skilled physician can readily determine and prescribe the effective amount of antineoplastic agent required to prevent, counter, or arrest the progress of the disease condition. For example, the adult dosage of temozolomide for an adult is generally about 150 $mg/m^2$ of body surface area.

The pharmaceutical formulation of the invention can be used for treating or preventing one or more diseases such as carcinoma, sarcoma, melanoma, glioma, glioblastoma, brain cancer, lung cancer, thyroid follicular cancer, pancreatic cancer, breast cancer, bladder cancer, myelodysplasia, anaplastic astrocytoma, prostate cancer, testicular cancer, anaplastic astrocytoma, colon and rectal cancer, lymphoma, leukemia, and mycosis fungoides.

The pharmaceutical formulation, its lyophilized powder, and the pharmaceutical formulation formed by reconstituting the lyophilized powder with at least one aqueous diluent can provide enhanced chemical stability. Enhanced chemical stability of the pharmaceutical formulation means the pharmaceutical formulation is stable in solution for at least 60 hours at room temperature (about 25° C.) and ambient light conditions. Enhanced chemical stability of the lyophilized powder means the lyophilized powder is suitable for storage from about 4° C. to about 40° C. preferably for about 12 months or more. Enhanced chemical stability of the pharmaceutical formulation formed by reconstituting the lyophilized powder with water or other aqueous diluent means the reconstituted lyophilized powder is stable in solution for about 48 hours or more at room temperature and ambient light conditions. One advantage of the stability of the lyophilized powder is extended pharmaceutical product shelf life. Extended pharmaceutical shelf life offers significant economic advantages.

In yet another embodiment, the present invention discloses stable pharmaceutical formulations comprising temozolomide and at least one dissolution enhancing agent sufficient to substantially dissolve temozolomide in at least one aqueous diluent. The dissolution enhancing agent can be urea, L-histidine, L-threonine, L-asparagine, L-serine, L-glutamine, or mixtures thereof. The pharmaceutical formulation comprising Temozolomide may have at least one other ingredient such as, for example, a bulking agent, buffer or pH adjuster, which are described above both as to their nature and amounts. Such pharmaceutical formulations can have the stability as discussed above. The invention additionally describes a process of preparing such stable pharmaceutical formulations.

In a further embodiment, the above-described formulations comprising Temozolomide can be lyophilized into a lyophilized powder and stored in a suitable container or such article of manufacture in a condition suitable to be reconstituted later at an appropriate time in water or other aqueous diluent(s) for administration to a patient in need of treatment as described above. The lyophilized powders can have long term storage stability as discussed above.

The stable pharmaceutical formulations and lyophilized forms comprising Temozolomide are described in more detail in the EXAMPLES section below.

The invention is therefore advantageous in that it allows the formation of a stable aqueous solution containing an antineoplastic agent. Other advantages include the ability of the pharmaceutical formulation to be lyophilized and stored as a lyophilized powder suitable to be reconstituted as an aqueous solution, which solution is suitable to be administered to a patient in need thereof.

The term "aseptic" means preventing microbial contamination.

The term "aqueous diluent(s)" means aqueous fluids suitable for injection into a patient. Non-limiting examples of aqueous diluents include water, normal saline, 5% dextrose solution, and other fluids suitable for injection into a patient, preferably suitable for intravenous injection into a patient.

Pharmaceutically acceptable salts suitable as acid addition salts as well as salts providing the anion of the quaternary salt include those prepared from acids such as hydrochloric, hydrobromic, phosphoric, sulfuric, maleic, citric, acetic, tartaric, succinic, oxalic, malic, glutamic, pamoic and the like, and other acids related to the pharmaceutically acceptable salts listed in *Journal of Pharmaceutical Science*, 66, 2 (1977).

The term "therapeutically effective amount" shall mean that amount of active ingredient that will elicit the biological or medical response of a tissue, system or animal that is being sought by a researcher or clinician.

The term "extended pharmaceutical shelf life" is intended to mean a shelf life for pharmaceutical products from about 12 months to about 18 months wherein there is a loss of no greater than 10% of the active agent when stored at recommended storage conditions. The active agent for this is invention is intended to mean the antineoplastic agent.

The term "patient" is intended to mean animals, mammals, humans, monkeys, rodents, domestic and farm animals.

The term "therapeutically effective amount" is intended to mean an amount of a therapeutic agent of the composition, such as temozolomide or other antineoplastic agents described above, that will have an antineoplastic effect on a tissue, system, animal or mammal that is being sought by the administrator (such as a researcher, doctor or veterinarian), which includes alleviation of the symptoms of the condition or disease being treated and the prevention, slowing or halting of progression of the neoplastic condition.

The term "weight percent" ("wt %") for purposes of this invention is calculated on a basis of total weight of the pharmaceutical formulation.

The term "Temozolomide" is intended to mean a compound having the formula:

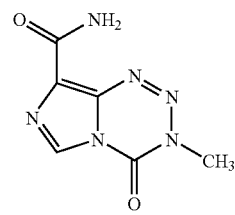

The synthesis of Temozolomide is well known. See, for example, Stevens et al., *J. Med. Chem*, 27, 196-201 (1984), and Wang et al., *J. Chem. Soc., Chem. Commun.*, 1687-1688 (1994) which are incorporated herein by reference.

EXAMPLES

The following examples have been set forth below as a guide to the practitioner and are not meant in any way to limit the scope of the present invention.

Example 1

The Pharmaceutical Formulation of the Invention is Generally Prepared by the Following Procedure 1. Urea or an amino acid with Polysorbate a bulking agent, and a buffer, is charged and dissolved in at least one aqueous diluent, wherein the amino acid is L-histidine, L-threonine, L-asparagine, L-serine, L-glutamine or mixtures thereof.
2. An antineoplastic agent is charged and dissolved into the solution from step 1. Dissolution of the antineoplastic agent is completed by mixing.
3. Water is added to the solution from step 2 to bring the batch to a volume with a desired solution density.
4. The solution from step 3 is aseptically filtered.

Example 2

For Batches A-D in Examples 2-5, the Actual Amount of Temozolomide to be Charged is Adjusted According to the Purity of the Drug Substance Batch Using the Following Formula grams Temozolomide=2.50×100/% Purity.

Sample Calculation:
Temozolomide drug substance=97.0% pure.
2.50×100/97.0=2.58 grams of Temozolomide to be charged for a 1-Liter batch.

For batches A-D in Examples 2-5, grams of concentrated Hydrochloric Acid (HCl) to be charged will be calculated as follows:

grams of concentrated HCL=100×(grams of HCl required)/% w/w Concentrated HCl

Sample Calculation:
Concentrated HCl=38.0% w/w

100×1.48/38.0=3.895 grams Concentrated HCl

1 L of Batch A was prepared by the procedure described below.

Batch A

| Ingredients | mg/ml | wt % |
|---|---|---|
| *Temozolomide | 2.50 | 8 |
| L-Threonine | 4.00 | 13 |
| Polysorbate 80 | 3.00 | 9 |
| Sodium Citrate Dihydrate | 5.88 | 19 |
| Mannitol | 15.0 | 48 |
| **Hydrochloric acid | 1.48 | 5 |
| Water for injection qs ad | 1.00 ml | |

Process of Manufacturing 1-Liter of Batch A Prior to Lyophilization
1. 4.00 g of L-Threonine, 3.00 g of polysorbate 80, 15 g of mannitol, 5.88 g of sodium citrate dihydrate, and 1.48 g of Hydrochloric acid, in that order, were charged and dissolved in water with agitation. The amount of water was about 80% of the total volume (batch volume).
2. *2.58 g of Temozolomide was charged and dissolved with agitation into the solution from Step 1. Complete dissolution of Temozolomide may require up to 2 hours of mixing.
3. **Water is added to bring the batch to the final volume with a solution density of 1.008±0.002 g/mL at 25° C. The solution was mixed for at least 15 minutes.
4. The solution was aseptically filtered through a sterilized 0.22 μm filter (Millipore, GVWP, Durapore), which was washed and tested for integrity, into a sterilized, stainless steel pressure vessel or equivalent. For a batch of 10 liters or less, a 293-mm membrane filter or equivalent was used. For batch sizes greater than 10 Liters, a 0.22 μm cartridge filter (MCGL40S Millidisk, Durapore GVWP) was used. The compounded batch can be stored at room temperature (19-25° C.) for up to 8 hours in a sealed, sterilized, stainless steel pressure vessel, and then refiltered following storage.
5. The solution from step 4 was aseptically filled into 20-mL Type 1 flint glass vials in aliquots of 10.7±0.2 mL. The vials were washed and sterilized prior to being filled.
6. 20-mm Daikyo D-713 lyo-shape rubber stoppers, which were washed, siliconized and sterilized, were aseptically inserted into the glass vials from step 5 in the lyophilization position.

Example 3

1 L of Batch B was Prepared by the Procedure Described Above Except that 2 g of L-Histidine was Used Instead of 4.00 g of L-Threonine, and 2.08 g of Hydrochloric Acid was Used Instead of 1.48 g of Hydrochloric Acid in Step 1

Batch B

| Ingredients | mg/ml | wt % |
|---|---|---|
| *Temozolomide | 2.50 | 8% |
| L-Histidine | 2.00 | 7% |

Batch B (-continued)

| Ingredients | mg/ml | wt % |
|---|---|---|
| Polysorbate 80 | 3.00 | 10% |
| Sodium Citrate dihydrate | 5.88 | 19% |
| Mannitol | 15.0 | 49 |
| **Hydrochloric acid | 2.08 | 7 |
| Water for injection qs ad | 1.00 ml | |

Example 4

1 L of Batch C was Prepared by the Procedure Described Above Except that 4 g of L-Asparagine was Used Instead of 4.00 g of L-Threonine in Step 1

Batch C

| Ingredients | mg/ml (except for water) | wt % |
|---|---|---|
| *Temozolomide | 2.50 | 8 |
| L-Asparagine | 4.00 | 13 |
| Polysorbate 80 | 3.00 | 9 |
| Sodium Citrate dihydrate | 5.88 | 19 |
| Mannitol | 15.0 | 48 |
| **Hydrochloric acid | 1.48 | 5 |
| Water for injection qs ad | 1.00 ml | |

Example 5

1 L of Batch D was Prepared by the Procedure Described Above Except that 5 g of Urea was Used Instead of 4.00 g of L-Threonine and 3.00 g of Polysorbate 80 in Step 1

Batch D

| Ingredients | mg/ml | wt % |
|---|---|---|
| *Temozolomide | 2.50 | 9 |
| Urea | 5.00 | 17 |
| Sodium Citrate dihydrate | 5.88 | 20 |
| Mannitol | 15.0 | 51 |
| **Hydrochloric acid | 1.48 | 5 |
| Water for injection qs ad | 1.00 ml | |

After lyophilization of batches A-D, the resulting powder was stored and, over a period of one week, four weeks, eight weeks and twelve weeks, the samples were reconstituted with water for analysis. The results are present in Table 1 below.

TABLE 1

| Batch # | Stability Time Point/Condition | % Initial Assay 1 | % Initial Assay 2 | Mean % Initial (n = 2) | Moisture (%) | Ph | Reconstitution Time (sec) |
|---|---|---|---|---|---|---|---|
| A | Initial | 100.00 | 100.00 | 100.00 | 0.4 | 3.75 | 30 |
| A | 1 week, LTC/LTR | 100.00 | 99.63 | 99.82 | 0.4 | 3.77 | 30 |
| A | 1 week, LTC/LTR Control | 100.11 | 99.99 | 100.05 | 0.4 | 3.77 | 30 |
| A | 4 week, 4 | 100.18 | 99.62 | 99.9 | 0.4 | 3.83 | 30 |
| A | 4 week, 25H | 100.24 | 99.13 | 99.69 | 0.3 | 3.84 | 30 |
| A | 4 week, 40 | 99.17 | 98.11 | 98.64 | 0.4 | 3.84 | 30 |
| A | 8 week, 25H | 99.43 | 98.82 | 99.125 | 0.4 | 3.81 | 30 |
| A | 12 week, 4 | 99.37 | 99.59 | 99.48 | 0.3 | 3.83 | 30 |
| A | 12 week, 25H | 99.24 | 99.22 | 99.23 | 0.4 | 3.82 | 30 |
| B | Initial | 100.00 | 100.00 | 100.00 | 1.6 | 3.96 | 30 |
| B | 1 week, LTC/LTR | 100.65 | 100.41 | 100.53 | 1.3 | 6.97 | 30 |
| B | 1 week, LTC/LTR Control | 99.63 | 100.27 | 99.95 | 1.6 | 3.97 | 30 |
| B | 4 week, 4 | 100.45 | 100.43 | 100.44 | 2.1 | 4.00 | 30 |
| B | 4 week, 25H | 99.89 | 99.04 | 99.47 | 2.0 | 4.00 | 30 |
| B | 4 week, 40 | 99.86 | 99.66 | 99.76 | 2.0 | 4.00 | 30 |
| B | 8 week, 25H | 99.91 | 100.15 | 100.03 | 2.0 | 4.04 | 30 |
| B | 12 week, 4 | 100.16 | 100.00 | 100.08 | 2.0 | 4.01 | 30 |
| B | 12 week, 25H | 98.84 | 100.2 | 99.52 | 2.0 | 4.00 | 30 |
| C | Initial | 100.00 | 100.00 | 100.00 | 0.3 | 4.00 | 30 |
| C | 1 week, LTC/LTR | 97.59 | 103.68 | 100.635 | 0.4 | 4.04 | 30 |
| C | 1 week, LTC/LTR Control | 98.14 | 99.55 | 98.845 | 0.5 | 4.04 | 30 |
| C | 4 week, 4 | 97.09 | 97.47 | 97.28 | 0.4 | 4.03 | 30 |
| C | 4 week, 25H | 98.49 | 97.18 | 97.835 | 0.5 | 4.03 | 30 |
| C | 4 week, 40 | 97.96 | 97.28 | 97.62 | 0.6 | 4.06 | 90 |
| C | 8 week, 25H | 98.42 | 97.56 | 97.99 | 0.6 | 4.04 | 30 |
| C | 12 week, 4 | 98.27 | 96.94 | 97.605 | 0.4 | 4.02 | 30 |
| C | 12 week, 25H | 98.67 | 97.77 | 98.22 | 0.6 | 4.02 | 30 |
| D | Initial | 100.00 | 100.00 | 100.00 | 0.4 | 4 | 30 |
| D | 1 week, LTC/LTR | 103.87 | 98.41 | 101.14 | 0.3 | 4.03 | 30 |
| D | 1 week, LTC/LTR Control | 100.46 | 98.95 | 99.705 | 0.4 | 4.02 | 30 |
| D | 4 week, 4 | 101.06 | 99.3 | 100.18 | 0.4 | 4.02 | 30 |
| D | 4 week, 25H | 101.69 | 98.97 | 100.33 | 0.4 | 4.02 | 30 |
| D | 4 week, 40 | 101.49 | 98.95 | 100.22 | 0.7 | 4.03 | 30 |
| D | 8 week, 25H | 100.86 | 98.78 | 99.82 | 0.5 | 4.01 | 30 |
| D | 12 week, 4 | 101.3 | 99.28 | 100.29 | 0.4 | 4 | 30 |
| D | 12 week, 25H | 101.37 | 98.59 | 99.98 | 0.5 | 4 | 30 |

The results show that the temozolamide in batches A-D was stable over one, four, eight and twelve week periods.

Example 6

Procedure for Lyophilization

The 20-mL glass vials from Examples 2-5, which were filled with the solution from one of Batches A-D, were placed into trays prior to lyophilization. Lyophilization was then carried out by the following procedure. A Lyostar Lyophilizer, which is manufactured by FTS systems, was used for the lyophilization.

1. Lyophilizer shelves were cooled to −50±5° C.
2. The trays of filled vials were aseptically loaded onto the lyophilizer shelves.
3. The lyophilizer shelves were held at a temperature of about 50±5° C. for 4.5 hours.
4. The lyophilizer shelves were warmed to about −22±2° C. in 1.5 hours and the product was maintained at a temperature of about −22±2° C. for at least 6 hours.
5. The shelves were cooled to about −50° C. in 3 hours and held at about −50±50° C. for 3 hours.
6. The condenser temperature was lowered to about −45° C. or below, and then the chamber was evacuated to about 100 μm Hg.
7. Once the chamber reached 100 μm Hg pressure, full vacuum (50-70 μM Hg) was applied and held for about 2 hours with the shelf temperature at about −50±5° C.
8. The pressure was changed to about 150 μm Hg and held for 30 minutes.
9. The shelves were heated to about 5° C. in 1 hour and 45 minutes. The shelf temperature was then maintained at about 5° C. for about 6 hours at approximately 150 μm Hg pressure.
10. The shelves were cooled to −2° C. in about 3 hours and the shelf temperature was maintained at about −2±2° C. for 32 hours at approximately 150 μm Hg pressure.
11. The shelves were heated to about 45° C. in 8 hours and maintained at a temperature of about 45±2° C. for about 5 hours at about 150 μm Hg pressure. The product temperature was then kept above −10° C.
12. The shelves were cooled to about 4° C. at a chamber pressure of about 150 μm and maintained at about 4° C. for a minimum of about 1 hour.
13. The chamber was vented with sterile filtered nitrogen to about 933 mBar.
14. The vials were stoppered inside the lyophilizer.
15. The chamber was vented with sterile filtered nitrogen to atmospheric pressure.
16. The vials were removed from the lyophilizer and crimped with 20-mm aluminum seals.
17. The vials were stored at about 2° to about 8° C. until inspection was completed.

It will be appreciated by those skilled in the art that changes could be made to the embodiments described above, including chemical and stereochemical changes, without departing from the broad inventive concept thereof. It is understood, therefore, that this invention is not limited to the particular embodiments disclosed, but it is intended to cover modifications which are within the spirit and scope of the invention, as defined by the appended claims.

What is claimed is:

1. A process of making a pharmaceutical formulation comprising the steps of:
   (i) dissolving at least one dissolution enhancing agent in at least one aqueous diluent wherein said dissolution enhancing agent is selected from the group consisting of L-histidine, L-threonine, L-asparagine, L-serine, and L-glutamine; and
   (ii) adding Temozolomide or a pharmaceutically acceptable salt thereof.

2. The process according to claim 1, wherein step (i) further comprises adding:
   a) a polysorbate;
   b) at least one bulking agent;
   c) at least one buffer; and
   d) at least one pH adjuster.

3. The process according to claim 1, or 2 further comprising lyophilizing the formulation to form a lyophilized powder.

4. The lyophilized powder, produced by the process of claim 3.

5. An article of manufacture comprising a container containing the lyophilized powder of claim 4.

6. The article of manufacture according to claim 5, wherein said container is a syringe or vial.

7. The article of manufacture according to claim 5, further comprising a volume of at least one aqueous diluent suitable for reconstitution of said lyophilized powder.

8. The process according to claim 1 or 2, wherein the dissolution enhancing agent is L-threonine.

9. The process according to claim 2, further comprising filtering said solution.

10. The process according to claim 2, wherein the bulking agent is mannitol.

11. The process according to claim 2, wherein the buffer is sodium citrate dihydrate.

12. The process according to claim 2, wherein the pH adjuster is hydrochloric acid.

13. The process according to claim 2, wherein the polysorbate is polysorbate 80.

14. The process according to claim 2, wherein: the dissolution enhancing agent is L-threonine, the bulking agent is mannitol, the buffer is sodium citrate dihydrate, the pH adjuster is hydrochloric acid, and the polysorbate is polysorbate 80.

15. The process according to claim 8, wherein Temozolomide is present in an amount ranging from about 4 wt % to about 16 wt %, and L-threonine is present in an amount ranging from about 8 wt % to about 20 wt %.

16. The process according to claim 14, wherein Temozolomide is present in an amount ranging from about 4 wt % to about 16 wt %, L-threonine is present in an amount ranging from about 8 wt % to about 20 wt %, mannitol is present in an amount ranging from about 40 wt % to about 56 wt %, sodium citrate dihydrate is present in amount ranging from about 15 wt % to about 28 wt %, hydrochloric acid is present in an amount ranging from about 4 wt % to about 8 wt %, and polysorbate 80 is present in an amount ranging from about 4 wt % to about 16 wt %.

17. The process according to claim 14, wherein Temozolomide is present in about 8 wt %, L-threonine is present in an about 13 wt %, mannitol is present in about 48 wt %, sodium citrate dihydrate is present in about 19 wt %, hydrochloric acid is present in about 5 wt %, and polysorbate 80 is present in about 9 wt %.

18. The process according to claim 17, further comprising lyophilizing the formulation to form a lyophilized powder.

19. The process according to claim 14, further comprising lyophilizing the formulation to form a lyophilized powder.

* * * * *